US012779113B2

(12) United States Patent
Ferner et al.

(10) Patent No.: US 12,779,113 B2
(45) Date of Patent: Nov. 3, 2026

(54) SYSTEM AND METHOD FOR DETECTING A FAULTY OCCLUDER VALVE

(71) Applicant: CareFusion 303, Inc., San Diego, CA (US)

(72) Inventors: Edward Stephen Ferner, Escondido, CA (US); Stephen D. Roberts, Lakeside, CA (US); Daniel M. Abal, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 1085 days.

(21) Appl. No.: 17/841,583

(22) Filed: Jun. 15, 2022

(65) Prior Publication Data

US 2022/0401646 A1 Dec. 22, 2022

Related U.S. Application Data

(60) Provisional application No. 63/212,441, filed on Jun. 18, 2021.

(51) Int. Cl.
*A61M 5/168* (2006.01)
*A61M 5/142* (2006.01)
*G16H 40/40* (2018.01)

(52) U.S. Cl.
CPC .... *A61M 5/16831* (2013.01); *A61M 5/14228* (2013.01); *G16H 40/40* (2018.01);
(Continued)

(58) Field of Classification Search
CPC ............ A61M 5/14228; A61M 60/284; A61M 2005/16863-16872; A61M 2205/3317
See application file for complete search history.

(56) References Cited

U.S. PATENT DOCUMENTS 5,478,211 A 12/1995 Dominiak et al.
5,842,841 A 12/1998 Danby et al.
(Continued)

FOREIGN PATENT DOCUMENTS

EP 3323447 A1 5/2018

OTHER PUBLICATIONS

Extended European Search Report for Application No. 22179600.6, dated Nov. 25, 2022, 11 pages.
(Continued)

*Primary Examiner* — Nathan R Price
(74) *Attorney, Agent, or Firm* — MASCHOFF BRENNAN

(57) ABSTRACT

An occluder detection system is disclosed. At least one occluder element moves according to a cam motion to apply a periodic compression to a flexible infusion line. A portion of the occluder element is configured to emit or modify an energy or magnetic field. A sensor is configured to measure the energy being emitted or modified by the section of the occluder element. A processor causes the at least one occluder element to move according to the cam motion to move a fluid within the flexible infusion line by periodically compressing the flexible infusion line, measures the energy of the energy source via the sensor, obtains a current cam state associated with the cam motion at a time corresponding to the measured energy, and determines, based on the measured energy and the current cam state, a state of the occluder element. The processor may issue an alarm on a fault condition.

19 Claims, 9 Drawing Sheets

(52) U.S. Cl.
CPC ............. *A61M 2005/16863* (2013.01); *A61M 2005/16868* (2013.01); *A61M 2005/16872* (2013.01); *A61M 2205/18* (2013.01); *A61M 2205/3306* (2013.01); *A61M 2205/3317* (2013.01)

(56) References Cited

U.S. PATENT DOCUMENTS

| | | | | |
|---|---|---|---|---|
| 9,677,555 | B2 | 6/2017 | Kamen et al. | |
| 2013/0177455 | A1 * | 7/2013 | Kamen .................. | G16H 20/17<br>417/313 |

OTHER PUBLICATIONS

European Office Action for Application No. 22179600.6, dated Jun. 30, 2026, 7 pages.

* cited by examiner

SYSTEM AND METHOD FOR DETECTING A FAULTY OCCLUDER VALVE

CROSS-REFERENCE TO RELATED APPLICATION

This application claims the benefit of U.S. Provisional Application No. 63/212,441, entitled "SYSTEM AND METHOD FOR DETECTING A FAULTY OCCLUDER VALVE," filed Jun. 18, 2021, the entirety of which is incorporated herein by reference.

TECHNICAL FIELD

This application relates generally to determining when an occluder valve operating on an intravenous (IV) administration line is failing or faulty.

BACKGROUND

As a result of the ongoing need for improved health care, there is a continuous effort with regard to administering intravenous fluid to patients. As is well known, medication dispensers and infusion devices are used for infusion of predetermined amounts of medication into the body of a patient. Various types of medication dispensers employing different techniques for a variety of applications are known to exist. Some existing infusion devices employ a finger type pump unit having fingers, often referred to in the industry as pumping fingers and occluder fingers (occluder valves), which are moved in predetermined sequence to fill and squeeze a tube to infuse predetermined amounts of medication continuously and cyclically into a patient. In many cases it is of critical importance to provide precisely controlled and consistent flow rates of intravenous fluid to patients. This need for more controlled IV flow rates is only partially fulfilled by the above-mentioned displacement pumps.

Infusion devices may monitor for some conditions that can negatively affect the accuracy and consistency of flow rates, such as by monitoring pressure sensors that indicate the occurrence of overpressures due to, for example, occlusions in the infusion line, which may cause interruptions in the infusion flow. Other conditions, such as a failing or faulty occluder valve, can also negatively affect flow rate accuracy and consistency. The delay between the detection of a condition negatively affecting flow accuracy and consistency and any subsequent alarm is relevant to patient safety.

SUMMARY

The subject technology modifies occlusion valves with various sensors to detect occlusion conditions in an intravenous (IV) administration line. The subject technology provides a medication infusion device having a finger-type pump unit which is small in size and light in weight and durable in construction.

According to various implementations, an occluder detection system comprises at least one occluder element configured to move according to a cam motion to apply a periodic compression to a flexible infusion line when the flexible infusion line is placed between the occluder element and a plate assembly, wherein a section of the occluder element is configured to emit or modify an energy or magnetic field; a sensor configured to measure the energy or magnetic field being emitted or modified by the section of the occluder element; one or more processors configured to: cause the at least one occluder element to move according to the cam motion to move a fluid within the flexible infusion line by periodically compressing the flexible infusion line; measure the energy or magnetic field via the sensor; obtain a current cam state associated with the cam motion at a time corresponding to the measured energy or magnetic field; determine, based on the measured energy or magnetic field, and the current cam state, a state of the occluder element; and cause, responsive to determining the state of the occluder element, an adjustment to a hardware element of a device associated with the flexible infusion line. Other aspects include corresponding methods, apparatuses, and computer program products for implementation of the foregoing features.

According to various implementations, an infusion pump comprises a first occluder element and a second occluder element each configured to move according to a cam motion to apply a periodic compression to a flexible infusion line when the flexible infusion line is placed between the occluder element and a plate assembly, wherein a portion of the occluder element is configured to emit or modify an energy or magnetic field; a first sensor and a second sensor each configured to measure the energy or magnetic field being emitted or modified by a respective first or second occluder element; and one or more processors configured to: cause the first and second occluder elements to move in a predetermined sequence according to the cam motion to squeeze the flexible infusion line to infuse predetermined amounts of medication continuously and cyclically into a patient; measure, using the first and second sensors, the energy or magnetic field emitted or modified by each occluder element; obtain a current cam state associated with the cam motion at a time corresponding to the measured energy; determine, based on the current cam state and determining a position of the respective occluder element based on the measured energy or magnetic field corresponding to the respective occluder element, a current linear displacement of each of the first and second occluder elements with respect to a predetermined expected position of the occluder element corresponding to the current cam state; determining that the current linear displacement of at least one of the first and second occluder elements did not correspond to a threshold compression of the flexible infusion line; and activate an alarm indicating that a respective occluder valve is defective responsive to determining that the current linear displacement did not correspond to the threshold compression of the flexible infusion line. Other aspects include corresponding systems, methods, apparatuses, and computer program products for implementation of the foregoing features.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Figure 1:
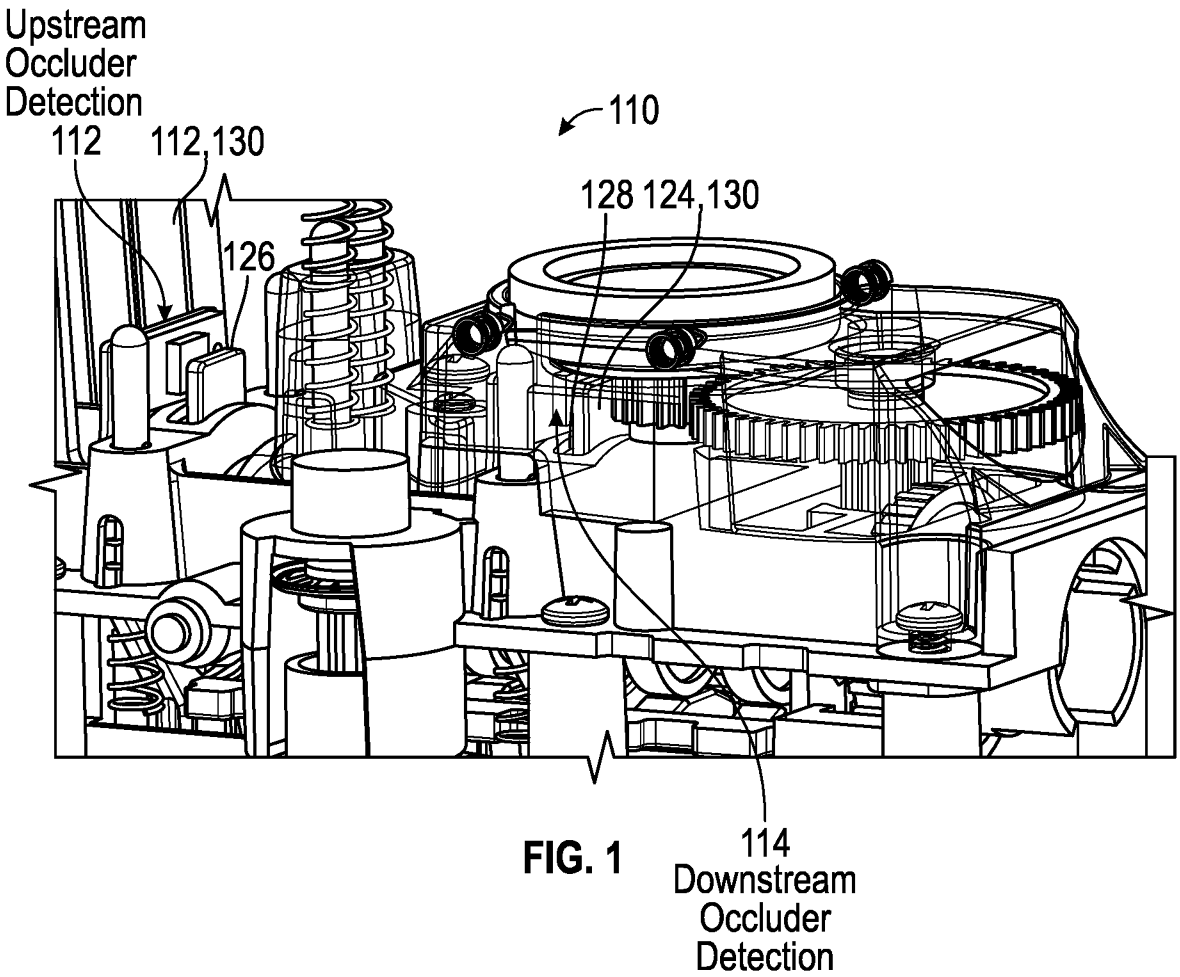
FIG. 1 depicts an example pumping mechanism of a large volume infusion pump including two occluder valves, according to various aspects of the subject technology.

FIG. 1 depicts an example pumping mechanism 110 of a large volume infusion pump including two occluder valves, according to various aspects of the subject technology. While a large volume infusion pump is depicted and used to describe the subject technology, the subject technology may be applied to numerous other pumps that utilize compression of tubing to effect the pumping action.

Infusion devices, such as those that include large volume infusion pumps (LVPs), may use a linear peristaltic or similar type of mechanism that creates the pumping action by way of squeezing the IV tubing to generate the pressure that causes the IV medication to flow through the IV tubing and ultimately into the patient. The squeezing action can also be used as a mechanism to close off the flow. This is used in pumping mechanisms that operate in a cyclical fashion by operating in a cycle that includes a filling portion and a delivery portion. In such instances, the pumping mechanism uses valving that includes an intake (or fill) valve 112, and an outflow (or delivery) valve 114. These valves can be referred to as "occluder valves". Proper operation of the pumping mechanism requires complete closure of these valves when they are not expected to be open. Incomplete closure will produce leakage, which can produce uncontrolled flow resulting in either, not enough medication, or too much medication being delivered to the patient. For this reason, it is desirable to verify that the occluder mechanism is operating as expected. Accordingly, the subject technology provides detection mechanisms for determining whether an upstream or downstream valve is faulty.

In order to verify that the valving mechanism is properly closing in an LVP pump, the degree of movement of the occluder has to extend past a certain point to ensure that the tubing is completely pinched (closed). If it is not, then there is a possibility of leaking and uncontrolled flow. The amount of occluder displacement is generally in the range of 15% to 20% of the tubing wall thickness. This ensures that the occluder will not lift under fluid pressure causing leakage. The force that is needed to be applied to the tubing to ensure that it is pinched, and closed, completely is therefore, important. In a system that generates the force using compression springs, the amount of force is dependent on the spring compression distance. By ensuring that the spring is compressed the correct amount, the occluder valve provides the required pinch force to the tubing.

Figure 3A:
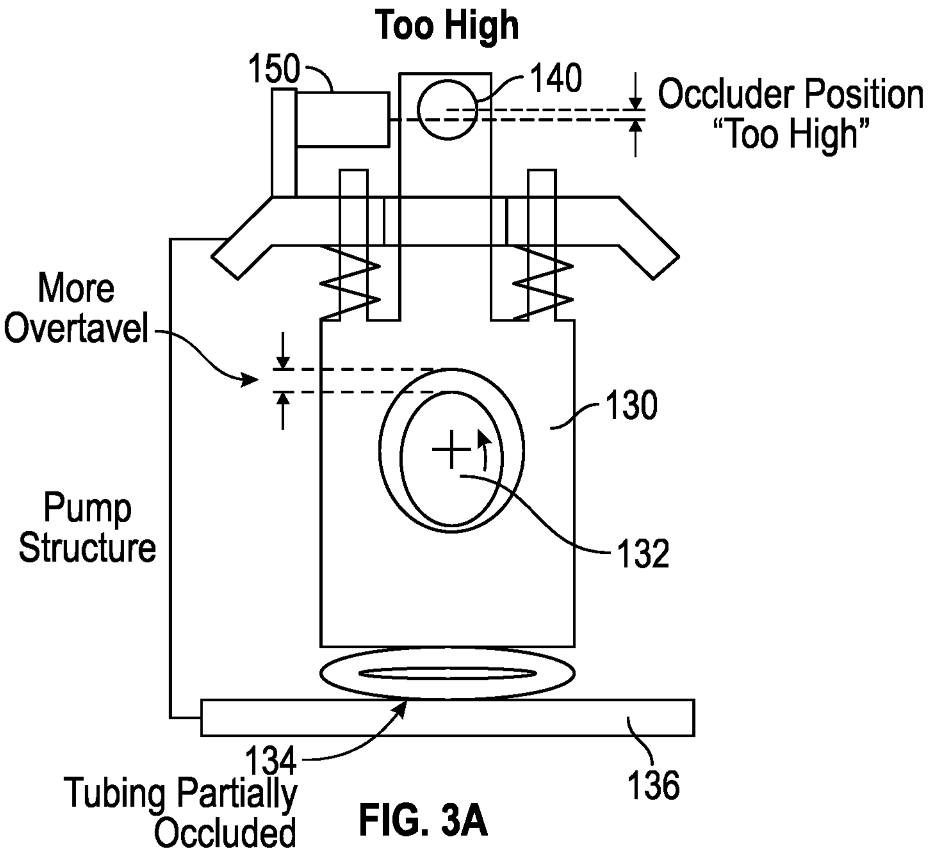
FIGS. 3A, 3B, and 3C depict various states of an occluder element having a magnetic element configured to be measured by a fixed external sensor, according to various aspects of the subject technology.
Figure 3B:
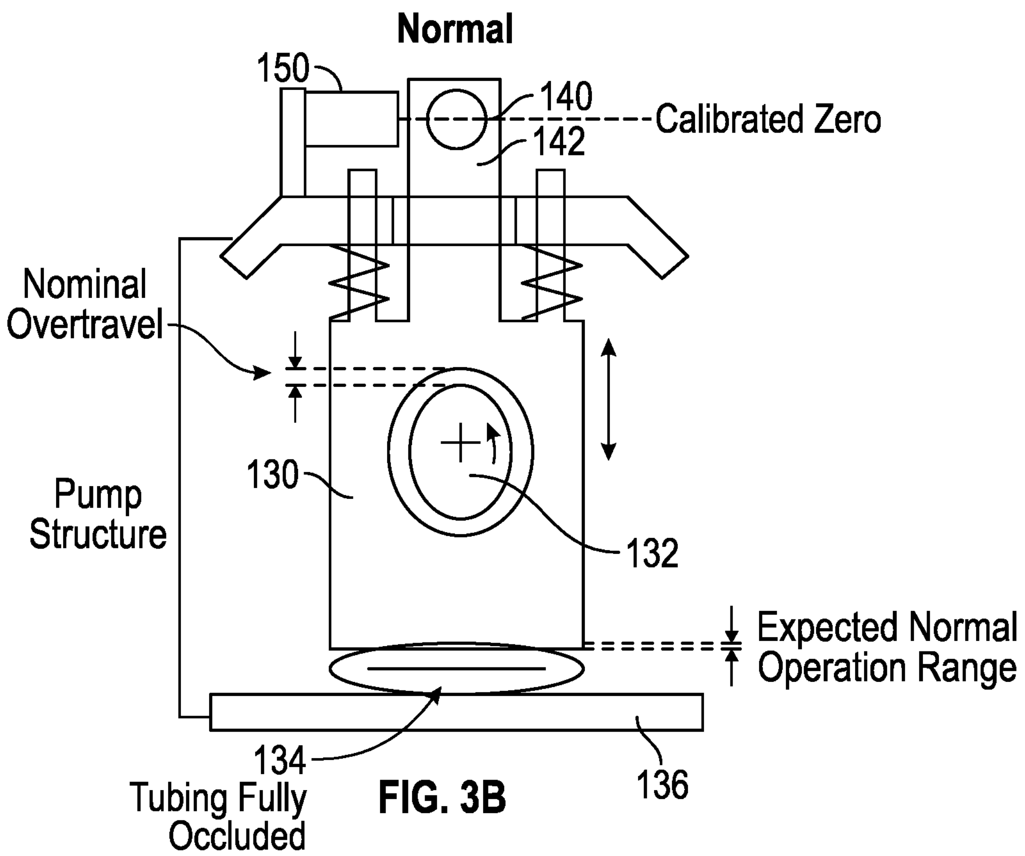

With brief reference to FIGS. 3A through 3B, infusion pumps may use a static member or plate assembly 136 (sometimes called a platen), and a moving member 130 (also called an occluder finger or occluder element) which compresses the tubing against the plate assembly to produce pinching and seals the fluid pathway. In the depicted example of FIG. 1, pumping mechanism 110 includes an upstream occluder element 122 and a downstream occluder element 124 slidably positioned in upstream valve 112 and downstream valve 114, respectively.

The pumping mechanism 110 comprises a cam assembly that acts upon the occluder elements 122, 124, and which is driven by an axle shaft (not shown). The axle shaft is driven by a motor and provides rotation to the cam assembly. The cam assembly may be formed and machined from a single piece of metal. The occluder elements 122, 124 may slidably move up and down and are subsequently displaced in a predetermined sequence, thereby squeezing a delivery tube placed between the occluder elements 122, 124 and dispensing a specified volume of fluid. According to various implementations each occluder valve may include a guide 126, 128 which at least partially constrains the occluder element therein. As shown in the depicted example, guides 126, 128 may include a slot in an upper portion of a housing, with a portion of the occluder element extending therethrough. As will be described further, guides 126, 128 may facilitate placement of an energy source or detection mechanism for determining a position and/or displacement of the respective occluder elements.

Figure 2A:
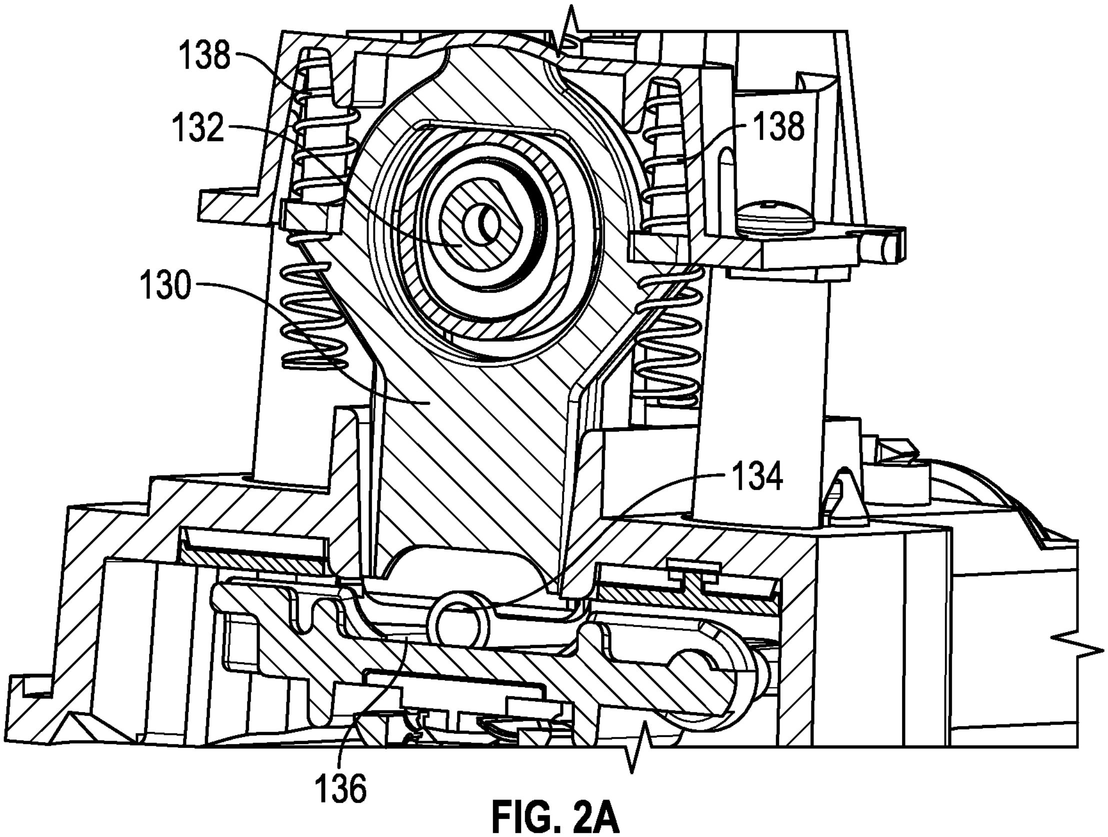
FIGS. 2A through 2C depict an example occluder element, according to various aspects of the subject technology.
Figure 2B:
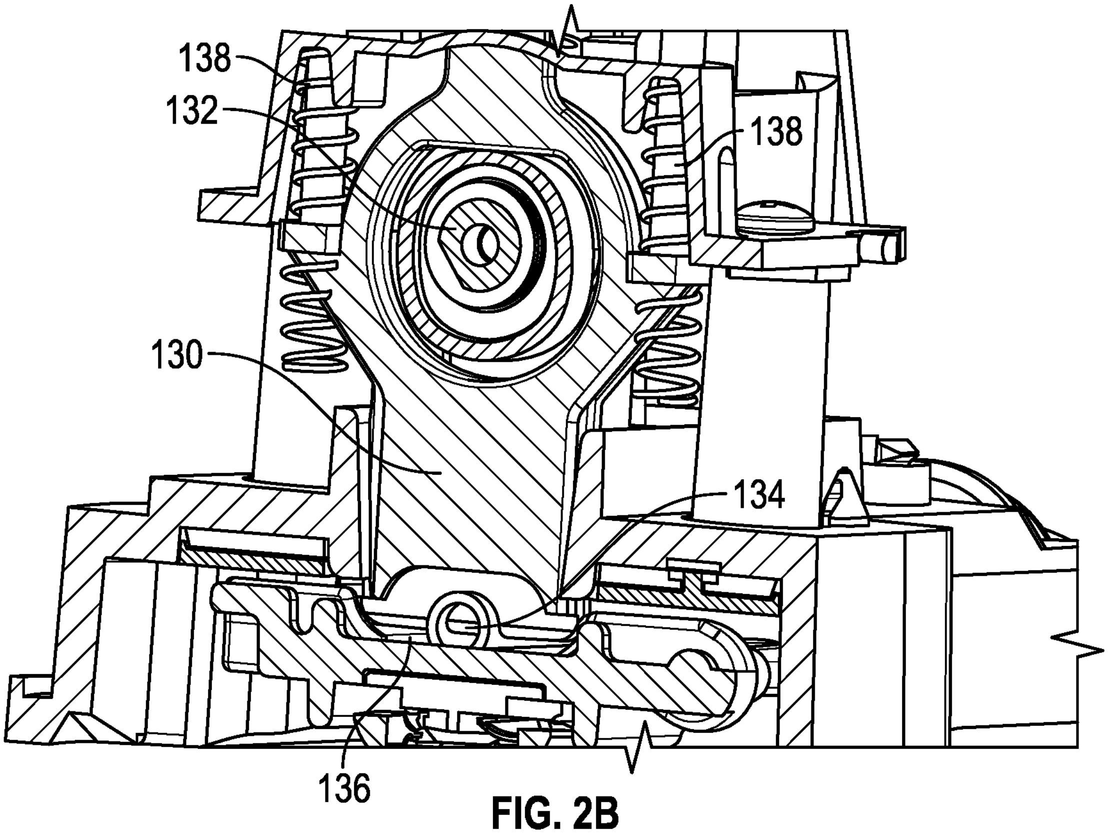
Figure 2C:
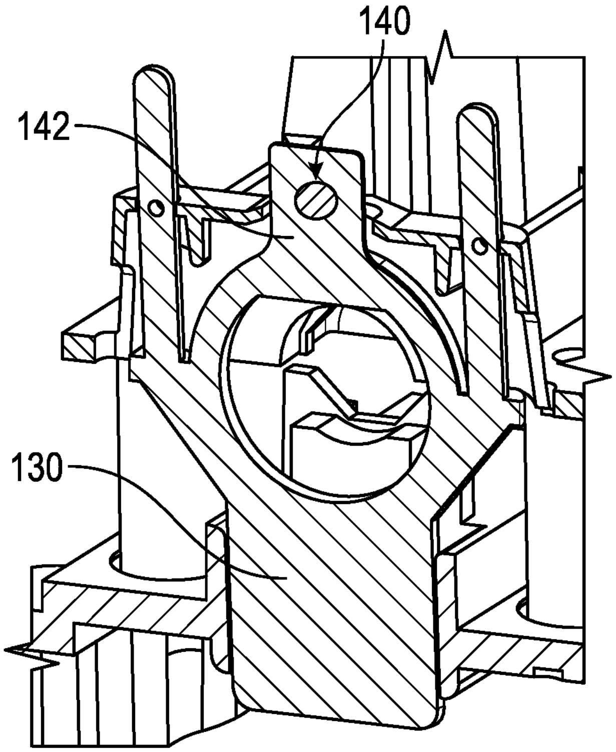

FIGS. 2A through 2C depict an example occluder element 130, according to various aspects of the subject technology. Occluder element 130 is configured to move according to a cam motion of a cam 132 to apply a periodic compression to a flexible infusion line 134 when the flexible infusion line is placed between the occluder element 130 and a plate assembly 136. In this regard, the cam motion oscillates the occluder element 130 to move a fluid within the flexible infusion line by periodically compressing the flexible infusion line. Compression springs 138 apply a constant force to the occluder element 130, forcing it against the plate assembly 136, while the cam 132 applies a force at predetermined intervals in an opposite direction, moving the lower portion of the occluder element responsible for compressing the infusion line 134 away from the plate assembly.

Each cam 132 may be elliptical in shape and may rotate on an axis off center of the ellipse. FIG. 2A depicts the occluder element 130 in the top dead center position (top position) with the stroke of the cam is fully upward and with the occluder element furthest apart from the plate assembly 136. FIG. 2B depicts the occluder element 130 is the bottom dead center position (lowest position) with the stroke of the cam being fully down and with the occluder element 130 closest to the plate assembly 136, thereby compressing an infusion line 134 when the infusion line is disposed in between the occluder element 130 and the plate assembly 136.

If the occluder is obstructed such as by fluid leaking into the mechanism and jamming the occluder, then it will not be able to achieve the full range of motion from top dead center position (TDC) to bottom dead center (BDC). The detection of the displacement of the occluder can be accomplished in many ways. By using electronic sensors that measure displacement by optical means, electromagnetic, or ultrasonic are some examples.

FIG. 2C depicts an example occluder element 130 with a magnetic element embedded therein. In such implementations, pumping mechanism 110 utilizes magnetism and an electromagnetic sensor. As in the depicted example, a magnet 140 may be placed on or embedded within the moving element 130 of the occluder valve. As will be described further, a sensor is placed in a fixed position on the pump mechanism 110 to measure an energy response from the magnet 140, and from that response determine a linear displacement of the occluder element 130 with respect to an expected position based on a current position of the cam 132.

According to various implementations the magnet 140 (or other similarly situated mechanism) may be placed on or embedded within an extension tab 142 extending from a top of the occluder element 130. As depicted in both FIGS. 1 and 2C, extension tab 142 may slidably move within a guide 126, 128.

Figure 3C:
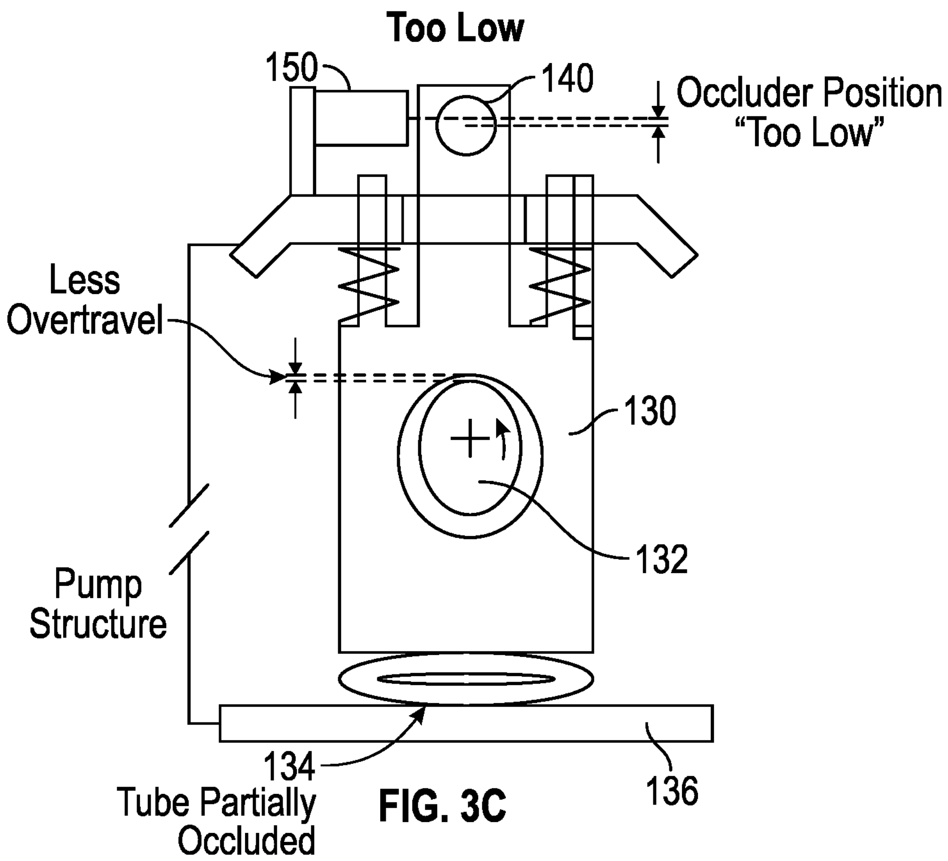

FIGS. 3A, 3B, and 3C depict various states of an occluder element 130 having a magnetic element configured to be measured by a fixed external sensor, according to various aspects of the subject technology. In the depicted example implementations, an occluder element 130 is configured to move according to a cam motion to apply a periodic compression to a flexible infusion line when the flexible infusion line is placed between the occluder finger and a plate assembly. FIGS. 3A and 3C depict examples in which the occluder element 130 has partially occluded the depicted tubing 134. In FIG. 3A, the occluder element 130 may experience more overtravel with respect to the cam 132, while in FIG. 3C, the occluder element 130 may experience less overtravel; while FIG. 3B may represent an example in which there is nominal overtravel experienced by the occluder element.

According to various implementations, a displacement sensing element 150 is connected to electronics that provide the necessary modulation and signal conditioning to provide an intelligible signal that can be used by the pump's software to determine the operating state of the occluder valve, and then make a decision as to whether or not to stop the pump and alarm notifying the user of an abnormal condition. In this regard, a sensor 150 is configured to measure an energy of the energy source being emitted or modified by an energy element of the occluder element 130.

In the depicted implementation, a section of the occluder element (e.g., an extension tab) is configured with a magnet to emit a magnetic field. The sensor 150 is externally fixed to an upper portion of a housing (e.g., a metal frame), as shown in both FIGS. 2 and 3. The sensor 150 is configured, for example by positioning, to measure a magnetic field emitted by the magnet 140. While the depicted example illustrates measuring a magnetic field, other energy sources and sensors may be used. For example, as will be described further, a photoelectric sensor may be used.

The sensor 150 provides signals to one or more processors of a monitoring circuit, for example, associated with or within the infusion pump. The processor(s) causes the occluder element 130 to move according to the cam motion to move a fluid within the flexible infusion line by periodically compressing the flexible infusion line. The processor (s) measure an energy or magnetic field modified or emitted by the occluder element 130, here a magnetic field.

Concurrently with measuring the energy field, the processor(s) obtains a current cam state associated with the cam motion at a time corresponding to the measured energy. For example, one or more sensors (not shown) may be configured to monitor a rotational positioning of cam 132. In this manner, the processor(s) is configured to determine when the cam 132 is at a top dead center (TDC) position or a bottom dead center (BDC) position. The processor(s) may then determine, based on the measured energy and the current cam state, a state of the occluder element 130. The state of the occluder element 130 may be a linear displacement from an expected position or, more generally, whether the occluder element is misaligned or displaced more than a threshold displacement.

The movement of the magnet creates a variable magnetic field which is proportional to the distance of the magnet to the sensor 150. In this way, the sensor outputs a value that is calibrated to be a certain position. In some implementations, the sensor 150 includes a Hall effect sensor. In some implementation, a linear inductive encoder may be used. In operation, two positions which represent the extended and retracted locations of the occluder element 130. Values received or derived from sensor measurements are used by a software algorithm that compares the values at these positions to acceptable values. If the values are outside the acceptable value, then the system has the capability of alarming the user of a fault, stopping the pump, or not allowing the pump to begin an infusion. This prevents the infusion pump from being used, thus preventing a serious over-infusion.

Using an AI (artificial intelligence or machine learning) algorithm, the occluder position data can also be compared against previous measurements from the instrument or compared to the population of pumps in the field, to identify abnormal conditions such as wear on the occluder mechanism. This can allow it to be used as a predictive measure to identify instruments that should be serviced, or taken out of use, prior to a failure occurring.

According to various implementations, the pumping mechanism 110 may be calibrated, such that the state of the occluder element (e.g., its position and/or fault condition) is determined based on the measured energy (e.g., magnetic field or light pattern) and the current cam state and a calibration parameter. The calibration parameter may be, for example, an offset value used in a calculation of the occluder element displacement, or a value used in the machine learning algorithm.

Accordingly, the infusion pump may be calibrated by performing an operation on the line set when the line set is first installed. The line set may be loaded and the calibration process started by way of the user inputting the necessary start procedure using the pump's interface, as discussed with regard to FIG. 7. The processor(s) may cause, prior to a normal operation of the occluder detection system, the at least one occluder element to move and apply an initial pressure to the flexible infusion line. The flexible infusion line may be empty with no fluid present, or may be primed with fluid. The processor(s) may then obtain a first measured energy corresponding to a first cam state when the initial pressure is applied, as discussed with regard to FIGS. 1 through 5, and then determine the calibration parameter based on the first measured energy.

Additionally or in the alternative, the state of the calibration parameter may result from user input at an input device. For example, the user may input the type of line set used, and the processor(s) may perform a lookup in memory (local or at a server) to determine a calibration parameter corresponding to the line set. In some implementations, the infusion device or other monitoring system may detect the line set automatically when installed (e.g., by way of an RFID embedded in the line set). In such implementations, user input may involve confirming the line set type once detected.

The occluder position detection system has the capability to identify various conditions, including obstructed movement of the occluder element 130, the detection of non-conforming IV pump tubing, mechanical component failure that affects positioning of the occluder stroke relative to the platen, and whether an object is lodged in the area of the occluder element.

For example, if the occluder element 130 is obstructed by fluid leaking into the mechanism and jamming the occluder, then it will not be able to achieve the full range of motion from TDC to BDC. Additionally, a software algorithm may be incorporated to measure the time interval between the TDC and BDC positions. This may be compared to the expected time interval calculated from the programmed flow rate. If this is outside the expected range, then it can indicate that the occluder is obstructed from movement. If a non-conforming IV set with tubing wall thickness that is over or under the required tolerances is used, the occluder position sensor will be able to identify be if the occluder does not reach the expected BDC position. If any object other than the tubing is placed in the area of the occluder such as another segment of the IV tubing, a piece of surgical tape etc. it would prevent the occluder to reach the BDC position and also limiting its range of motion which would be detected by the sensor.

If the occluder element 130 is too high, for example with respect to the sensor 150, the occluder element may exhibit significant overtravel with respect to the cam 132, as depicted in FIG. 3A. In these situations, the tubing may be only partially occluded, and failure modes may include a broken or missing spring, stuck occluder finger, foreign object, or non-concentric tubing. On the other hand, if the occluder element 130 is too low, for example with respect to the sensor 150, the occluder element may exhibit less than nominal overtravel with respect to the cam 132. In these situations, the tubing may only be partially occluded, and failure modes may include a broken and/or missing platen, a broken door hinge, a foreign object, or a cracked bezel boss, among other failures. Any of the foregoing situations may be detected and reported by the processor(s).

The foregoing detection mechanism provides the numerous advantages. For example, a means to detect the correct functioning of the occluder elements is provided in real-time. Fault conditions may be detected that could lead to uncontrolled flow causing inadvertent over or under infusion of medication to patient. The system can further potentially detect wear of the occlusion mechanism and identify instruments that may need repair.

Figure 4:
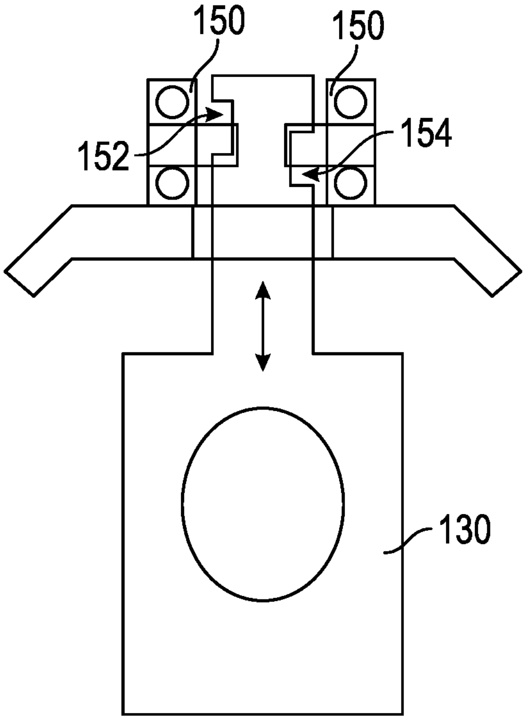
FIG. 4 depicts an example occluder element configured to be measured by one or more photo electric sensors, according to various aspects of the subject technology.

FIG. 4 depicts an example occluder element 130 configured to be measured by one or more photo electric sensors 150, according to various aspects of the subject technology. The depicted implementation uses photo electric sensors 150 to determine if the valve is in the correct position. Accordingly, the system uses an emitter detector pair with an emitter that emits light onto the detector. The occluder finger has a feature molded onto it which is referred to a flag. The flag is made of a material that is opaque to the light of the emitter. The purpose of the flag is then to indicate to the detector the position of the occluder. The emitter/detector sensor is mounted in one position relative to the flag to determine if the occluder is fully extended to the required position. Another emitter/detector sensor can be located to determine the fully retracted position of the occluder.

When the light path is obstructed, the detector will output a binary "on" signal, when unobstructed the sensor will not detect light and output an "off" signal. These values are then used by the software to determine the state of the occluder during operation. The software will only check the sensor status at the positions when the occluder is either fully extended (closed), and fully retracted (open). The software will determine if the correct logic signal is provided by the sensor. If the logic signal is off, then this indicates that the occluder is not in the correct position, or that the sensor is malfunctioning. In both of these cases, the software can then alarm the user of the fault, stopping the pump or not allowing the pump to begin an infusion.

Figure 5A:
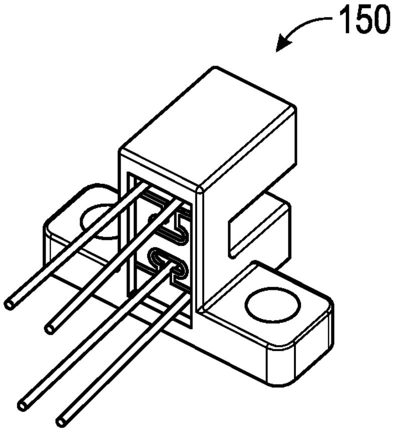
FIG. 5A depicts example photelectric elements such as those used in FIG. 4.

FIG. 5A depicts an example photelectric element such as those used in FIG. 4. In such configurations, the sensor element 150 may include both an emitter as well as a receiver. In some implementations, the occluder or its extension tab 142 may be notched, with each notch providing a light path for determining a position of the occluder element 130. FIG. 4 depicts an implementation in which two sensors used to measure two respective notches; a first notch 152 for detecting when the occluder is too high, and a second notch 154 for detecting when the occluder is too low. In this regard, a light-based trigger threshold is satisfied when a respective notch allows light to pass through the notch (e.g., indicating a high or low depending on the notch that is triggered). According to some implementations, there can be some vertical travel (e.g., 0.010") wherein both sensors 150 are below the trigger threshold.

Figure 5B:
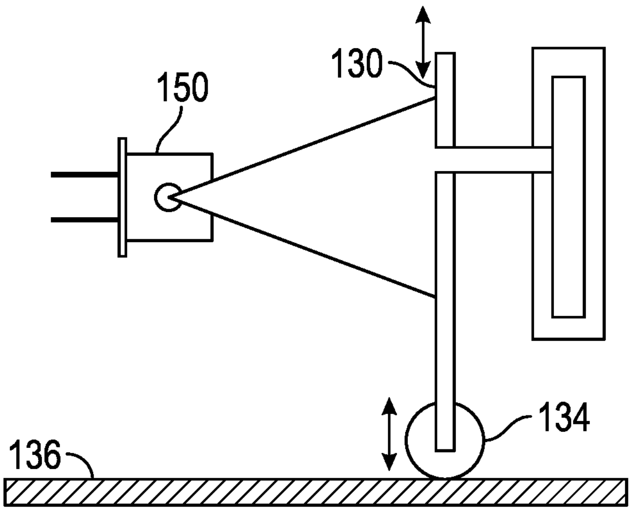
FIG. 5B depicts an example photoelectric detection implementation.

Various other photoelectric configurations may be used. For example, FIG. 5B depicts an example uniform light emission pattern configuration. In FIG. 5B, a light emitting diode (LED) is used to project a uniform emission pattern against a portion of the occluder element. The occluder element includes a slit which allows a portion of the light to pass through. This portion of light is then measured by an optical encoder strip which encodes a position of the occluder element based on where the light is sensed. Other examples include providing a visual flag (e.g., painted lines or stripes) on the occluder element which can then be read by an optical sensor, and the position determined based on the shape and/or size and/or color of the flag that is read at any particular time.

Figure 5C:
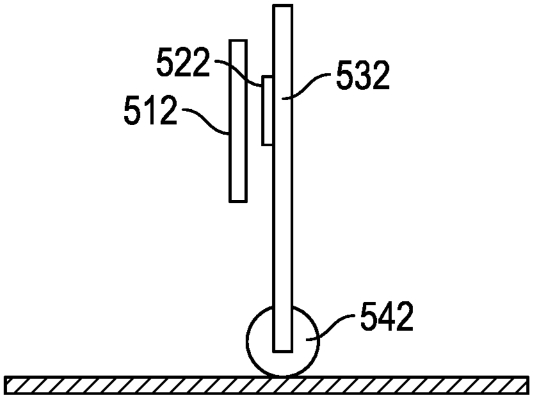
FIG. 5C depicts an example linear encoder implementation.

FIG. 5C depicts an example linear encoder implementation. The example shown in FIG. 5C includes a magnetic detector 512 positioned proximate to an inductive element 522. The inductive element 522 may be positioned on an occluder valve 532 that can compress a fluid tube 542. The magnetic detector 512 may sense the position of the inductive element 522. Based on the position, the faulty occluder valve may be detected. In some implementations, the magnetic detector 512 may additionally or alternatively sense the strength of the magnetic field interacting with the inductive element 522. The strength can be used to detect whether the occluder valve 532 is positioned perpendicular (or in other predetermined pumping position) to the fluid tube 542. If the strength is greater or less than expected, or non-uniform, the occluder valve 532 may be off center or angled (e.g., broken or bent). Examples of the magnetic detector 512 include a linear encoder or Hall effect sensor.

Figure 6:
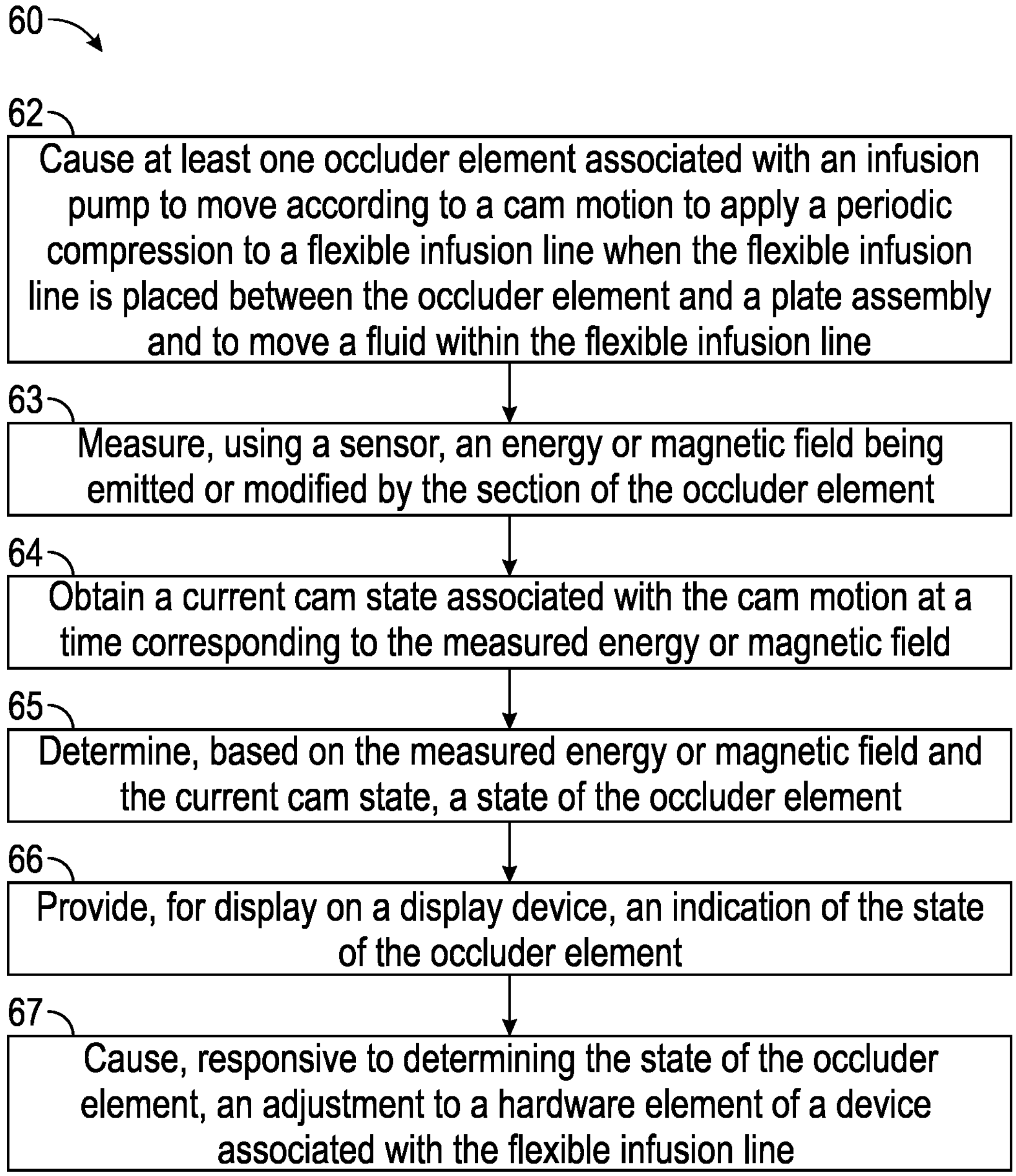
FIG. 6 depicts an example process for detecting a faulty occluder valve, according to aspects of the subject technology.

FIG. 6 depicts an example process 60 for detecting a faulty occluder valve, according to aspects of the subject technology. For explanatory purposes, the various blocks of example process 60 are described herein with reference to FIGS. 1 through 5, and the components and/or processes described herein. The one or more of the blocks of process 60 may be implemented, for example, by one or more computing devices including, for example, within infusion device 12 of FIG. 7. In some implementations, one or more of the blocks may be implemented based on one or more machine learning algorithms. In some implementations, one or more of the blocks may be implemented apart from other blocks, and by one or more different processors or devices. Further for explanatory purposes, the blocks of example process 60 are described as occurring in serial, or linearly. However, multiple blocks of example process 60 may occur in parallel. In addition, the blocks of example process 60 need not be performed in the order shown and/or one or more of the blocks of example process 60 need not be performed.

In the depicted example, a processor (or processors) associated with an infusion device causes at least one occluder element (e.g., occluder element 130) associated with an infusion pump to move according to a cam motion to apply a periodic compression to a flexible infusion line when the flexible infusion line is placed between the occluder element and a plate assembly and to move a fluid within the flexible infusion line (62). As described previously, the occluder element may be configured to emit or modify an energy. For example, the occluder element may be a magnetic element embedded in a portion of the occluder element such as an extension tab 142.

The processor measures, using a sensor, an energy or magnetic field being emitted or modified by the section of the occluder element (63). For example, the sensor may be a magnetic sensor to detect a magnetic field. As examples, sensor may be a Hall effect sensor or a linear inductive encoder configured to measure a position of the magnetic object with respect to the sensor. The sensor may be configured to measure a magnetic flux emitted by the magnetic object. Additionally, or in the alternative, the sensor may be a photoelectric sensor configured to measure a position at least one occluder element based on detecting a diffusion characteristic of a light transmitted through a portion of the occluder element.

The processor obtains a current cam state associated with the cam motion at a time corresponding to the measured energy (64), and determines, based on the measured energy or magnetic field and the current cam state, a state of the occluder element (65). The state of the occluder element may be determined, for example, based on a magnitude and/or direction of a measured magnetic flux. Determining the state of the occluder element may include, for example, determining a linear displacement of the occluder element from a predetermined expected position of the occluder element corresponding to the current cam state.

Figure 7:
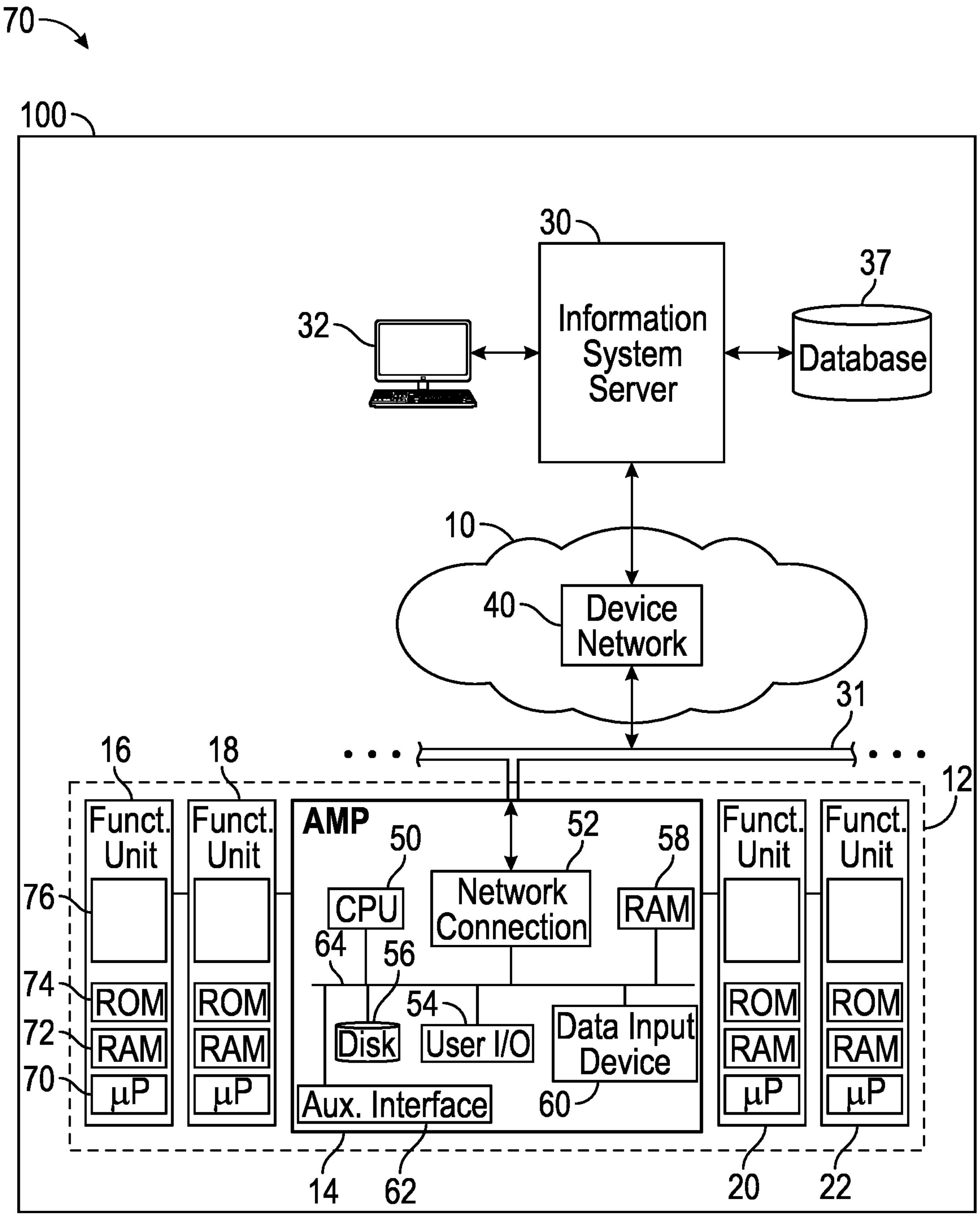
FIG. 7 depicts an example diagram of an institutional patient care device of a healthcare organization, according to aspects of the subject technology.

The processor then (optionally) provides, for display on a display device (e.g., display device 54 or display screen of device 16 or 32 of FIG. 7), an indication of the state of the occluder element (66). In some implementations, the processor may determine that the linear displacement of the occluder element did not correspond to a threshold compression of the flexible infusion line, and provide an alarm (or alert). The alarm may indicate, for example, that an occluder valve corresponding to the occluder element is defective or faulty, and/or that the compression of the flexible infusion line did not correspond to the threshold compression. The processor then (optionally) causes, responsive to determining the state of the occluder element, an adjustment to a hardware element of a device associated with the flexible infusion line (67). According to various implementations, the hardware element may include a cam of the infusion pump.

According to various implementations, the processor(s) may cause first and second occluder elements, such as shown in FIG. 1, to move in a predetermined sequence to squeeze the flexible infusion line to infuse predetermined amounts of medication continuously and cyclically into a patient. The processor(s) may obtain, using first and second sensors, a current state of each of the first and second occluder elements based on the current cam state and position of each magnetic object with respect to each respective sensor. In such implementations, the alarm may be activated responsive to determining that the linear displacement of at least one of the first and second occluder elements did not correspond to the threshold compression of the flexible infusion line.

Many of the above-described devices, systems and methods, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

FIG. 7 depicts an example diagram of an institutional patient care device 70 of a healthcare organization, according to aspects of the subject technology. In FIG. 7, a patient care device (or "medical device" generally) 12 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. As described previously, PCU/PCD 12 (and/or the infusion pump) functions as the previously described reporter 104.

Each device 12 may be connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1 optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 40 by which patient care devices 12 (and other devices) communicate in accordance with normal operations.

Additionally, institutional patient care system 70 may incorporate a separate information system server 30. According to various implementations, server 30 and/or database 37 may incorporate, function as, or include a remote records system configured to store electronic medication administration records (eMAR) for patients admitted or cared for within the hospital organization. Although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, mobile devices such as laptops, tablet computers, augmented reality devices, or smartphones, configured with software for communications with information system server 30 via network 10.

Patient care device 12 comprises a system for providing patient care, such as for providing an infusion of medication to a patient. Patient care device 12 may include or incorporate an infusion pump, a physiological monitor (e.g., heart rate, blood pressure, ECG, EEG, pulse oximeter, and other patient monitors), therapy device, and other drug delivery device. In the depicted example, patient care device 12 comprises a control unit 14, also referred to as interface unit 14 or docking station, connected to one or more functional modules 16, 18, 20, 22. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally, or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1 to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with controller 14, or any other system on the network, using suitable programming and communication protocols.

Network connection 52 may be a wired or wireless connection, such as by Ethernet, WiFi, BLUETOOTH, an integrated service digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 7, at least one of functional modules 16, 18, 20, 22 may be an infusion pump module such as an intravenous infusion pump for delivering medication or other fluid to a patient. For the purposes of this discussion, functional module 16 is an infusion pump module, and includes the forgoing pumping mechanism 10 including occluder valves. Each of functional modules 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 18, 20 and/or 22 may be a printer, scanner, bar code reader or any other peripheral input, output or input/output device.

Each functional module 16, 18, 20, 22 may communicate directly or indirectly with interface unit 14, with interface unit 14 providing overall monitoring and control of device 12. Functional modules 16, 18, 20, 22 may be connected physically and electronically in serial fashion to one or both ends of interface unit 14 as shown in FIG. 7. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information and performing the functions and/or operations described herein. It should be noted that while four functional modules are shown in FIG. 7, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 16.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Patient care device 12 is capable of operating in several different modes, or personalities, with each personality defined by a configuration database. The configuration database may be a database 56 internal to patient care device, or an external database 37. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in HIS server 30, decision support 48, remote data server 49, hospital department or unit stations 46, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices, and maintain open communication.

With further reference to FIG. 7, an infusion device, as used herein, may be a patient care device 12, interface control unit 14, or a module 16, 18, 20, 22. According to various implementations, the infusion device includes a pump and a control unit. The control unit 14 is configured to provide, using the pump, an intravenous infusion of a medication to a current patient, and display on a display screen, while the infusion is being provided by the pump, a representation of a status of the intravenous infusion.

Figure 8:
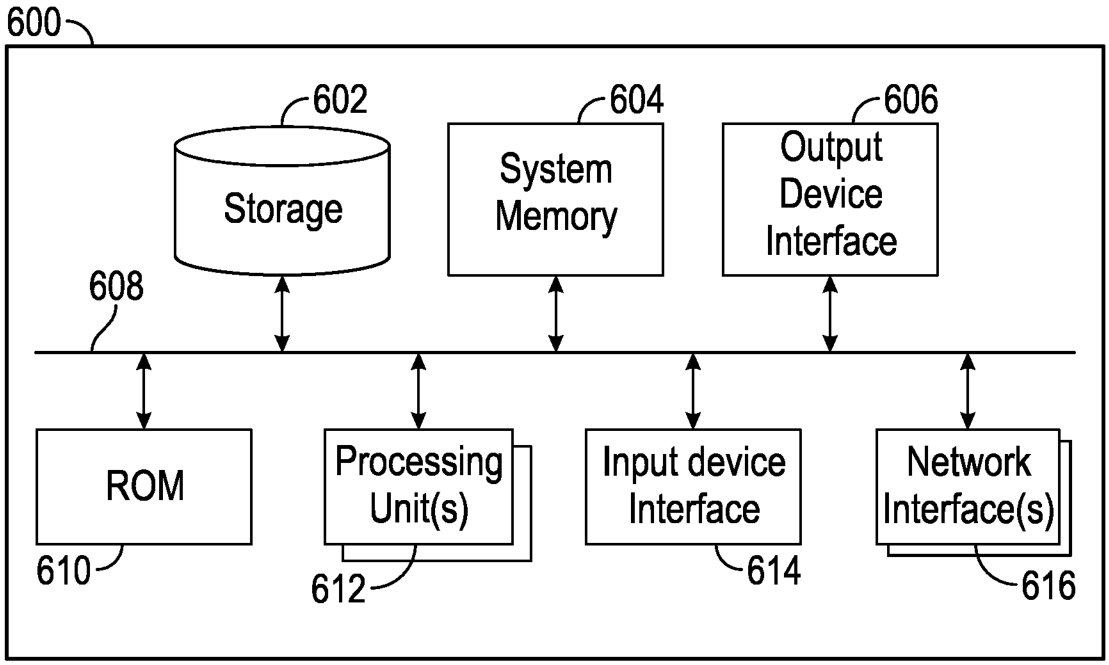
FIG. 8 is a conceptual diagram illustrating an example electronic system for detecting a faulty occluder valve, according to aspects of the subject technology.

FIG. 8 is a conceptual diagram illustrating an example electronic system 600 for detecting a faulty occluder valve, according to aspects of the subject technology. Electronic system 600 may be a computing device for execution of software associated with one or more components and processes provided by FIGS. 1 to 7, including but not limited to controller 406, or computing hardware within pump 401 or system 330. Electronic system 600 may be representative of a device used in connection or combination with the disclosure regarding FIGS. 1 to 7. In this regard, electronic system 600 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 600 may include various types of computer readable media and interfaces for various other types of computer readable media. In the depicted example, electronic system 600 includes a bus 608, processing unit(s) 612, a system memory 604, a read-only memory (ROM) 610, a permanent storage device 602, an input device interface 614, an output device interface 606, and one or more network interfaces 616. In some implementations, electronic system 600 may include or be integrated with other computing devices or circuitry for operation of the various components and processes previously described.

Bus 608 collectively represents all system, peripheral, and chipset buses that communicatively connect the numerous internal devices of electronic system 600. For instance, bus 608 communicatively connects processing unit(s) 612 with ROM 610, system memory 604, and permanent storage device 602.

From these various memory units, processing unit(s) 612 retrieves instructions to execute and data to process in order to execute the processes of the subject disclosure. The processing unit(s) can be a single processor or a multi-core processor in different implementations.

ROM 610 stores static data and instructions that are needed by processing unit(s) 612 and other modules of the electronic system. Permanent storage device 602, on the other hand, is a read-and-write memory device. This device is a non-volatile memory unit that stores instructions and data even when electronic system 600 is off. Some implementations of the subject disclosure use a mass-storage device (such as a magnetic or optical disk and its corresponding disk drive) as permanent storage device 602.

Other implementations use a removable storage device (such as a floppy disk, flash drive, and its corresponding disk drive) as permanent storage device 602. Like permanent storage device 602, system memory 604 is a read-and-write memory device. However, unlike storage device 602, system memory 604 is a volatile read-and-write memory, such a random access memory. System memory 604 stores some of the instructions and data that the processor needs at runtime. In some implementations, the processes of the subject disclosure are stored in system memory 604, permanent storage device 602, and/or ROM 610. From these various memory units, processing unit(s) 612 retrieves instructions to execute and data to process in order to execute the processes of some implementations.

Bus 608 also connects to input and output device interfaces 614 and 606. Input device interface 614 enables the user to communicate information and select commands to the electronic system. Input devices used with input device interface 614 include, e.g., alphanumeric keyboards and pointing devices (also called "cursor control devices"). Output device interfaces 606 enables, e.g., the display of images generated by the electronic system 600. Output devices used with output device interface 606 include, e.g., printers and display devices, such as cathode ray tubes (CRT) or liquid crystal displays (LCD). Some implementations include devices such as a touchscreen that functions as both input and output devices.

Also, as shown in FIG. 8, bus 608 also couples electronic system 600 to a network (not shown) through network interfaces 616. Network interfaces 616 may include, e.g., a wireless access point (e.g., Bluetooth or WiFi) or radio circuitry for connecting to a wireless access point. Network interfaces 616 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 600 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML, page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all implementations, or one or more implementations. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. An occluder detection system, comprising:

at least one occluder element configured to move according to a cam motion of a cam to apply a periodic compression to a flexible infusion line when the flexible infusion line is placed between the occluder element and a plate assembly, wherein a section of the occluder element is slidably movable within at least a portion of a guide which at least partially constrains the occluder element at a location separate from the cam, the section of the occluder element being configured to emit or pass through an energy or magnetic field;

a sensor configured to measure the energy or magnetic field being emitted or modified by the section of the occluder element;

one or more processors configured to:

cause the at least one occluder element to move according to the cam motion to move a fluid within the flexible infusion line by periodically compressing the flexible infusion line;

measure the energy or magnetic field via the sensor;

obtain a current cam state associated with the cam motion at a time corresponding to the measured energy or magnetic field;

determine, based on the measured energy or magnetic field, and the current cam state, a state of the occluder element; and cause, responsive to determining the state of the occluder element, an adjustment to a hardware element of a device associated with the flexible infusion line.

2. The occluder detection system of claim 1, further comprising:

an infusion pump, wherein the hardware element is a cam of the infusion pump.

3. The occluder detection system of claim 1, wherein the occluder element comprises a magnetic object configured to emit the magnetic field, and wherein the sensor is configured to measure a magnetic field emitted by the magnetic object, and wherein the state of the occluder element is determined based on a magnitude and direction of the measured magnetic field.

4. The occluder detection system of claim 1, wherein the occluder element comprises a magnetic object configured to emit the magnetic field, and wherein the sensor is a hall effect sensor or a linear inductive encoder configured to measure the magnetic field of the magnetic object and determine position of the magnetic object with respect to the sensor based on the measured magnetic field.

5. The occluder detection system of claim 1, wherein the one or more processors are further configured to:

provide, for display on a display device, an indication of the state of the occluder element.

6. The occluder detection system of claim 5, wherein the section of the occluder element is an extension tab constrained by the portion of the guide, wherein determining the state of the occluder element comprises:

determining, based on the measured energy or magnetic field, a linear displacement of the occluder element from a predetermined expected position of the occluder element corresponding to the current cam state.

7. The occluder detection system of claim 6, wherein the occluder detection system further comprises:

an infusion pump, wherein the one or more processors are further configured to:

determine that the linear displacement of the occluder element did not correspond to a threshold compression of the flexible infusion line, wherein providing the indication of the state of the occluder element comprises activating an alarm indicating that an occluder valve corresponding to the at least one occluder element is defective.

8. The occluder detection system of claim 7, wherein the at least one occluder element comprises a first occluder element and a second occluder element, and wherein the occluder detection system further comprises:

a first sensor configured to measure a first energy or magnetic field being emitted by or passing through the first occluder element;

a second sensor configured to measure a second energy or magnetic field being emitted by or passing through the second occluder element;

wherein the one or more processors are further configured to:

cause the first and second occluder elements to move in a predetermined sequence to squeeze the flexible infusion line to infuse predetermined amounts of medication continuously and cyclically into a patient; and obtain a current state of each of the first and second occluder elements based on the current cam state and based on determining a position of the respective occluder element based on the measured energy or magnetic field corresponding to the respective occluder element, wherein the alarm is activated responsive to determining that the linear displacement of at least one of the first and second occluder elements did not correspond to the threshold compression of the flexible infusion line.

9. The occluder detection system of claim 6, wherein the state of the occluder element is determined based on the measured energy or magnetic field and the current cam state and a calibration parameter, wherein the one or more processors are further configured to:

cause, prior to a normal operation of the occluder detection system, the at least one occluder element to move and apply an initial pressure to the flexible infusion line; and obtain a first measured energy or magnetic field corresponding to a first cam state when the initial pressure is applied; and determine the calibration parameter based on the first measured energy or magnetic field.

10. The occluder detection system of claim 1, wherein the state of the occluder element is determined based on the measured energy or magnetic field and the current cam state and a calibration parameter, wherein the one or more processors are further configured to:

receive the calibration parameter as a result of a user input at an input device.

11. The occluder detection system of claim 1, wherein the sensor is a photoelectric sensor configured to measure a position of the at least one occluder element based on detecting a diffusion characteristic of a light transmitted through the section of the at least one occluder element, and wherein determining the state of the occluder element comprises:

determining a linear displacement of the occluder element from a predetermined expected position of the occluder element corresponding to the current cam state.

12. A machine-implemented method, performed by an occluder detection system, comprising:

causing at least one occluder element associated with an infusion pump to move according to a cam motion of a cam to apply a periodic compression to a flexible infusion line when the flexible infusion line is placed between the occluder element and a plate assembly and to move a fluid within the flexible infusion line, wherein a section of the occluder element is slidably movable within at least a portion of a guide which at least partially constrains the occluder element at a location separate from the cam, the section of the occluder element being configured to emit or pass through an energy or magnetic field;

measuring, using a sensor, the energy or magnetic field being emitted or modified by the section of the occluder element;

obtaining a current cam state associated with the cam motion at a time corresponding to the measured energy or magnetic field;

determining, based on the measured energy or magnetic field and the current cam state, a state of the occluder element;

causing, responsive to determining the state of the occluder element, an adjustment to a hardware element of a device associated with the flexible infusion line; and providing, for display on a display device, an indication of the state of the occluder element.

13. The machine-implemented method of claim 12, wherein the occluder element comprises a magnetic object configured to emit the magnetic field, and wherein the sensor is a hall effect sensor or a linear inductive encoder configured to measure the magnetic field of the magnetic object and determine position of the magnetic object with respect to the sensor based on the measured magnetic field.

14. The machine-implemented method of claim 13, wherein the section of the occluder element is an extension tab constrained by the portion of the guide, wherein determining the state of the occluder element comprises:

determining, based on the measured energy or magnetic field, a linear displacement of the occluder element from a predetermined expected position of the occluder element corresponding to the current cam state.

15. The machine-implemented method of claim 14, further comprising:

determining that the linear displacement of the occluder element did not correspond to a threshold compression of the flexible infusion line, wherein providing the indication of the state of the occluder element comprises activating an alarm indicating that an occluder valve corresponding to the at least one occluder element is defective.

16. The machine-implemented method of claim 15, wherein the at least one occluder element comprises a first occluder element and a second occluder element, the method further comprising:

causing the first and second occluder elements to move in a predetermined sequence to squeeze the flexible infusion line to infuse predetermined amounts of medication continuously and cyclically into a patient;

obtaining, using first and second sensors, a current state of each of the first and second occluder elements based on the current cam state and based on determining a position of the respective occluder element based on the measured energy or magnetic field corresponding to the respective occluder element, wherein the alarm is activated responsive to determining that the linear displacement of at least one of the first and second occluder elements did not correspond to the threshold compression of the flexible infusion line.

17. The machine-implemented method of claim 12, wherein the state of the occluder element is determined based on the measured energy or magnetic field and the current cam state and a calibration parameter, wherein the method further comprises:

causing, prior to a normal operation of the infusion pump, the at least one occluder element to move and apply an initial pressure to the flexible infusion line; and obtaining a first measured energy or magnetic field corresponding to a first cam state when the initial pressure is applied; and determining the calibration parameter based on the first measured energy or magnetic field.

18. The machine-implemented method of claim 12, wherein the state of the occluder element is determined based on the measured energy or magnetic field and the current cam state and a calibration parameter, the method further comprising:

receiving the calibration parameter as a result of a user input at an input device.

19. An infusion pump, comprising:

a first occluder element and a second occluder element each configured to move within a respective occluder valve according to a cam motion of a cam to apply a periodic compression to a flexible infusion line when the flexible infusion line is placed between the respective occluder element and a plate assembly, wherein a section of the respective occluder element is slidably movable within at least a portion of a guide which at least partially constrains the respective occluder element at a location separate from the cam, the section of the respective occluder element being configured to emit or pass through an energy or magnetic field;

a first sensor and a second sensor each configured to measure the energy or magnetic field being emitted or passed through a respective first or second occluder element;

one or more processors configured to:

cause the first and second occluder elements to move in a predetermined sequence according to the cam motion to squeeze the flexible infusion line to infuse predetermined amounts of medication continuously and cyclically into a patient;

measure, using the first and second sensors, the energy or magnetic field emitted or modified by each occluder element;

obtain a current cam state associated with the cam motion at a time corresponding to the measured energy or magnetic field;

determine, based on the current cam state and determining a position of the respective occluder element based on the measured energy or magnetic field corresponding to the respective occluder element, a current linear displacement of each of the first and second occluder elements with respect to a predetermined expected position of the respective occluder element corresponding to the current cam state;

determine that the current linear displacement of at least one of the first and second occluder elements did not correspond to a threshold compression of the flexible infusion line; and activate an alarm indicating that a respective occluder valve is defective responsive to determining that the current linear displacement did not correspond to the threshold compression of the flexible infusion line.

* * * * *